United States Patent [19]

Handte et al.

[11] Patent Number: 4,602,932
[45] Date of Patent: Jul. 29, 1986

[54] USE OF QUINOLYLOXY COMPOUNDS AS ANTIDOTES FOR FENOXAPROP-ETHYL (ETHYL-2-(4-(6-CHLOROBENZOX-AZOLYLOXY)-PHENOXY)-PROPIONATE)

[75] Inventors: Reinhard Handte, Gablingen; Hilmar Mildenberger, Kelkheim; Klaus Bauer, Rodgau; Hermann Bieringer, Eppstein/Taunus, all of Fed. Rep. of Germany

[73] Assignee: Hoechst Aktiengesellschaft, Frankfurt, Fed. Rep. of Germany

[21] Appl. No.: 698,559

[22] Filed: Feb. 6, 1985

[30] Foreign Application Priority Data

Feb. 8, 1984 [DE] Fed. Rep. of Germany ....... 3404401

[51] Int. Cl.$^4$ ...................... A01N 43/42; A01N 43/76
[52] U.S. Cl. ............................................. 71/88; 71/94
[58] Field of Search ...................................... 71/88, 94

[56] References Cited

U.S. PATENT DOCUMENTS 3,133,810 5/1964 Hamm .................. 71/100

FOREIGN PATENT DOCUMENTS 94349 11/1983 European Pat. Off. ............... 71/94

OTHER PUBLICATIONS

Hubele, "Use of Quinoline Derivatives, etc.," (1983) CA 100:103194d (1984).
Hoechst, "Herbicidal Composition" (1979), CA 92:175774g, (1980).
Bieringer et al., "Enhancement of Carbohydrate, etc." (1982), CA 97:34711s (1982).

Primary Examiner—Glennon H. Hollrah
Assistant Examiner—Andrew Duff Meikle
Attorney, Agent, or Firm—Curtis, Morris & Safford

[57] ABSTRACT

Compounds of the formula

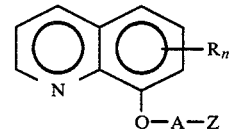

I in which A denotes $-CH_2-$ or $-CH(CH_3)-$ and Z denotes a carboxyl group or a (thio)carboxylic ester group, are effective antidotes for the herbicide Fenoxaprop-ethyl.

15 Claims, No Drawings

USE OF QUINOLYLOXY COMPOUNDS AS ANTIDOTES FOR FENOXAPROP-ETHYL (ETHYL-2-(4-(6-CHLOROBENZOXAZOLYLOXY)-PHENOXY)-PROPIONATE)

It is already known from EP A-94,349 that, inter alia, quinolyloxyalkanecarboxylic acid derivatives can be used to protect crop plants against the harmful side effects of agricultural chemicals, in particular herbicides.

It has now been found that the said compounds are excellently suitable for broadening the spectrum of use of Fenoxaprop-ethyl, i.e. ethyl-2-[4-(6-chlorobenzoxazolyloxy)phenoxy]-propionate.

The present invention therefore relates to the use of quinolyloxy compounds of the formula

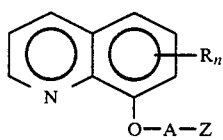

in which
A denotes $-CH_2-$ or $-CH(CH_3)-$,
R denotes halogen, in particular chlorine,
Z denotes $COOR_1$ or $COSR_2$,
$R^1$ denotes H or $(C_1-C_8)$-alkyl which can be substituted by halogen or $(C_1-C_4)$-alkoxy; $(C_3-C_6)$-alkenyl, $(C_3-C_6)$-alkinyl or a cation equivalent of an inorganic or organic base;
$R^2$ denotes $(C_1-C_4)$-alkyl and
n denotes a number from zero to two,
as safeners for the herbicide ethyl 2-[4-(6-chlorobenzoxazolyloxy)-phenoxy]-propionate(II).

"Cation equivalents" above are to be understood as meaning, in particular, alkali or alkaline earth metal ions and also ammonium which is optionally monosubstituted to trisubstituted by lower alkyl and hydroxyalkyl.

The compounds of the formula I are known for the most part or can be prepared by generally known processes (cf. EP A-94,349).

A number of compounds of the formula I are listed as examples in the table below:

TABLE

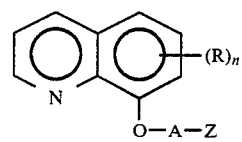

| Example | $(R)_n$ | A | Z | m.p. (°C.) |
|---|---|---|---|---|
| 1 | H | $CH_2$ | COOH | 232 |
| 2 | 5-Cl | $CH_2$ | COOH | 104–5 |
| 3 | 5-Cl | $CH_2$ | $COOCH_3$ | 63–6 |
| 4 | 5-Cl | $CH_2$ | $COOC_4H_9$ (tert.) | 97–8 |
| 5 | 5-Cl | $CH_2$ | $COOC_2H_4OCH_3$ | 87–8 |
| 6 | 5-Cl | $CH_2$ | $COOC_8H_{17}(n)$ | 98–9 |
| 7 | 5-Cl | $CH_2$ | $COOCH_2CH=CH_2$ | |
| 8 | 5,7-Di-Cl | $CH_2$ | COOH | |
| 9 | 5,7-Di-Cl | $CH_2$ | $COOC_2H_5$ | |
| 10 | 5,7-Di-Cl | $CH_2$ | $COOC_6H_{13}$ | |
| 11 | 5,7-Di-Cl | $CH_2$ | $COOCH_2-CH_2-OCH_3$ | |
| 12 | 5,7-Di-Cl | $CH_2$ | $COOCH_2-C\equiv CH$ | |
| 13 | 5,7-Di-Cl | $CH_2$ | $COOCH_2-CH_2-CH_2-Cl$ | |
| 14 | 5,7-Di-Cl | $CH_2$ | $COOCH_3$ | 65 |
| 15 | 5,7-Di-Cl | $CH_2$ | COONa | |
| 16 | 5,7-Di-Cl | $CH_2$ | COOK | |
| 17 | 5,7-Di-Cl | $CH_2$ | $COSC_2H_5$ | |
| 18 | H | $CH_2$ | $COOCH_3$ | 70 |
| 19 | H | $CH_2$ | $COOC_4H_9(n)$ | |
| 20 | 5-Cl | $CH_2$ | $COOCH_2C\equiv CH$ | 115–6 |
| 21 | 5-Cl | $CH_2$ | $COOCH_2CH_2CH_2Cl$ | |
| 22 | 5-Cl | $CH(CH_3)$ | COOH | |
| 23 | 5-Cl | $CH(CH_3)$ | $COOCH_3$ | |
| 24 | 5-Cl | $CH(CH_3)$ | $COOC_4H_9(n)$ | |
| 25 | 5-Cl | $CH(CH_3)$ | $COOC_2H_5$ | |
| 26 | 5,7-Di-Cl | $CH(CH_3)$ | COOH | |
| 27 | 5,7-Di-Cl | $CH(CH_3)$ | $COOC_3H_7(i)$ | |
| 28 | 5,7-Di-Cl | $CH(CH_3)$ | $COONH_4$ | |
| 29 | 5,7-Di-Cl | $CH(CH_3)$ | $COONH(C_2H_5)_3$ | |

The compounds of the general formula I are distinguished by the fact that they are applied in low, i.e. subtoxic, concentrations in conjunction with Fenoxapropethyl(II) and are then capable of antagonizing, i.e. completely eliminating, harmful side effects of the latter, without impairing its herbicidal effectiveness.

As a result of this the field of use of the agent can be increased considerably. The present invention also relates, therefore, to a process for protecting crop plants against phytotoxic side effects of II, which comprises treating the plants, parts of plants or fertile soils for plants with a compound of the formula I before, after or at the same time as II.

II is used above all for combating grass-like weeds in dicotyledonous crops, for example soya and potatoes. In monocotyledonous crops, such as, for example, cereals, rice and maize, Fenoxaprop-ethyl can, however, only be employed to a limited extent.

As a result of the combination, according to the invention, with a safener of the formula I, the herbicide can also be used as a selective agent for combating grass-like weeds in monocotyledonous crop plants, in particular species of cereals, such as wheat, barley, rice and sorghum.

The antidote:herbicide ratio can vary within wide limits between 0.1 and 5 parts of antidote to 1 part of herbicide. The optimum ratio depends on the antidote and on the nature of the crop of plants to be treated. Preferably the weight ratio antidote:herbicide is (0.2–2) to 1.

Depending on their properties, the safeners can be used for pretreating the seed of the crop plant (seed dressing) or can be introduced into the seed furrows before sowing or can be used together with the herbicide before or after the emergence of the plants. Preemergence treatment includes both the treatment of the cultivated area before sowing and the treatment of cultivated areas which have been sown but are not yet covered with vegetation.

In principle, the antidote can be used before, after or at the same time as the herbicide, but its simultaneous use in the form of tank mixtures or finished formulations is preferred.

For application, the compounds of the formula I can be made up with customary formulation auxiliaries to give dusting agents, wettable powders, dispersions, emulsion concentrates, granules or microgranules which contain the active compound in a concentration of 2-80% and are either used as such (dusting agents or pellets) or are dissolved or dispersed in a solvent (water) before use.

Wettable powders are preparations which are uniformly dispersible in water and which, in addition to the active compound, also contain, apart from a diluent or inert substance, if appropriate, wetting agents, for example polyoxyethylated alkylphenols, polyoxethylated fatty alcohols, alkylsulfonates or alkylphenylsulfonates and dispersing agents, for example sodium ligninsulfonate, sodium 2,2'-dinaphthylmethane-6,6'-disulfonate, sodium dibutylnaphthalenesulfonate or sodium oleoylmethyltauride. Preparation is effected in a customary manner, for example by grinding and mixing the components.

Emulsifiable concentrates can be prepared, for example, by dissolving the active compound in an inert organic solvent, for example butanol, cyclohexanone, dimethylformamide, xylene or higher-boiling aromatic compounds or hydrocarbons with the addition of one or more emulsifiers. In the case of liquid active compounds, the solvent component can be omitted wholly or partly. The following are examples of emulsifiers which can be used: calcium alkylarylsulfonates, such as Ca dodecylbenzenesulfonate, or nonionic emulsifiers, such as polyglycol esters of fatty acids, alkylaryl polyglycol ethers, fatty alcohol polyglycol ethers, propylene oxide/ethylene oxide condensation products, fatty alcohol/propylene oxide ethylene oxide condensation products, alkyl polyglycol ethers, sorbitan esters of fatty acids, polyoxethylenesorbitan esters of fatty acids or esters of polyoxethylenesorbitol.

Dusting agents can be obtained by grinding the active compound with finely divided solid substances, for example talc, natural clays, such as kaolin, bentonite or pyrophillite, or diatomaceous earth.

Granules can be prepared either by atomizing the active compound onto an adsorptive, granulated inert material or by applying concentrations of active compounds to the surface of carriers, sucu as sand or kaolinite, or granulated inert material by means of binders, for example polyvinyl alcohol, sodium polyacrylate or mineral oils. Suitable active compounds can also be granulated in the manner customary for the production of fertilizer granules, if desired as a mixture with fertilizers.

In wettable powders the concentration of active compound is, for example, about 10 to 90% by weight, the remainder up to 100% by weight is composed of customary formulation ingredients. In the case of emulsifiable concentrates, the concentration of active compound can be about 10 to 80% by weight. Formulations in the form of dusts contain in most cases 5 to 20% by weight of active compound, while atomizable solutions contain about 2 to 20% by weight. In the case of granules, the content of active compound depends partly on whether the active compound is in a liquid or solid state and on the granulation auxiliaries, fillers etc. which are used.

In addition, the active compound formulations mentioned contain, if appropriate, the tackifiers, wetting agents, dispersing agents, emulsifiers, penetration agents, solvents, fillers or carriers which are customary in a particular case.

For application, the concentrates, present in a commercial form, are optionally diluted in a customary manner, for example by means of water in the case of wettable powders, emulsifiable concentrates and dispersions and, in part, also in the case of microgranules. Preparations in the form of dusts and granules and also atomizable solutions are usually not diluted further with further inert substances before application.

A. FORMULATION EXAMPLES a. A dusting agent is obtained by mixing 10 parts by weight of safener and 90 parts by weight of talcum or inert substance and comminuting the mixture in a beater mill.

b. A wettable powder which is readily dispersible in water is obtained by mixing 25 parts by weight of safener, 64 parts by weight of kaolin-containing quartz as an inert substance, 10 parts by weight of potassium (ligninsulfonate and 1 part by weight of sodium oleoylmethyltauride as a wetting and dispersing agent, and grinding the mixture in a pinned disk mill.

c. A dispersion concentrate which is readily dispersible in water is obtained by mixing 20 parts by weight of safener with 6 parts by weight of an alkylphenol polyglcyol ether (Triton X 207), 3 parts by weight of isotridecanol polyglycol ether (8 EO) and 71 parts by weight of paraffinic mineral oil (boiling range, for example, approx. 255° to over 377° C.), and grinding the mixture in a ball mill to a fineness less than 5 microns.

d. An emulsifiable concentrate is obtained from 15 parts by weight of safener, 75 parts by weight of cyclohexanone as solvent and 10 parts by weight of oxethylated nonylphenol as emulsifier.

B. BIOLOGICAL EXAMPLES

EXAMPLE 1

Wheat, barley and 2 important weeds (Avena fatua and Alopecurus myosuroides) were sown and cultivated under greenhouse conditions to the 4-leaf stage. Safeners according to the invention and Fenoxapropethyl(II) were then sprayed onto the test plants in various dosages. After a waiting period in the greenhouse of 4 weeks more, the plants were examined to check for any kind of inhibition or damage in comparison with test plants not treated with safeners. The results show that the safeners reduce very greatly or completely eliminate the herbicidal harmful effects on wheat and barley, without impairing the herbicidal effectiveness against the weeds Avena and Alopecurus.

The safener action of the quinoline derivatives in various crops of cereals:

| Product | Dosage kg of active ingredient/ hectare | Herbicidal action, % | | | | |
|---|---|---|---|---|---|---|
| | | TA | TD | HV | ALM | AVF |
| Fenoxaprop- ethyl(II) | 0.8 | 20 | 98 | 95 | — | — |
| | 0.4 | 10 | 94 | 87 | 98 | 96 |
| | 0.2 | 5 | 85 | 81 | 93 | 86 |
| | 0.1 | 0 | 57 | 43 | 87 | 42 |
| II + compound 18 | 0.8 + 0.2 | 2 | 0 | 67 | — | — |
| | 0.4 + 0.1 | 0 | 0 | 52 | 99 | 95 |
| | 0.2 + 0.05 | 0 | 0 | 51 | 90 | 87 |
| | 0.1 + 0.025 | 0 | 0 | 32 | 83 | 51 |
| II + compound 3 | 0.8 + 0.4 | 0 | 0 | 5 | — | — |
| | 0.8 + 0.2 | 0 | 0 | 15 | — | — |
| | 0.4 + 0.2 | 0 | 0 | 0 | 100 | 98 |

-continued

| Product | Dosage kg of active ingredient/ hectare | Herbicidal action, % | | | | |
| --- | --- | --- | --- | --- | --- | --- |
| | | TA | TD | HV | ALM | AVF |
| | 0.4 + 0.1 | 0 | 0 | 2 | 98 | 96 |
| | 0.2 + 0.1 | 0 | 0 | 0 | 92 | 89 |
| | 0.2 + 0.05 | 0 | 0 | 0 | 90 | 91 |
| | 0.1 + 0.05 | 0 | 0 | 0 | 85 | 56 |
| | 0.1 + 0.025 | 0 | 0 | 0 | 80 | 30 |
| II + compound 14 | 0.8 + 0.2 | 0 | 60 | 69 | — | — |
| | 0.4 + 0.1 | 0 | 57 | 67 | 99 | 96 |
| | 0.2 + 0.05 | 0 | 52 | 53 | 95 | 93 |
| | 0.1 + 0.025 | 0 | 25 | 22 | 86 | 57 |
| II + compound 1 | 0.8 + 0.2 | 0 | | | — | — |
| | 0.4 + 0.1 | 0 | | | 96 | 94 |
| | 0.2 + 0.05 | 0 | | | 93 | 88 |
| | 0.1 + 0.025 | 0 | | | 60 | 40 |
| II + compound 2 | 0.8 + 0.2 | 0 | 10 | 15 | — | — |
| | 0.4 + 0.1 | 0 | 0 | 10 | 98 | 96 |
| | 0.2 + 0.05 | 0 | 0 | 10 | 87 | 85 |
| | 0.1 + 0.025 | 0 | 0 | 0 | 77 | 47 |

Abbreviations:
TA = Triticum aestivum
HV = Hordeum vulgare
TD = Triticum durum
ALM = Alopecurus myosuroides
AVF = Avena fatua

We claim:

1. A method for protecting grasslike crop plants against the phytotoxic side effects of Fenoxaprop-ethyl, i.e. ethyl 2-[4-(6-chlorobenzoxazolyloxy)-phenoxy]-propionate, which method comprises applying to said plants, to parts of said plants, or to fertile soil for said plants, before, after, or simultaneously with said Fenoxaprop-ethyl, an effective amount of a compound of the formula

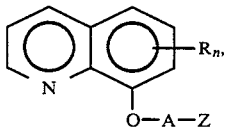

wherein
A is —CH$_2$— or —CH(CH$_3$)—;
R is halogen;
Z is —COOR$^1$;
R$^1$ is H or (C$_1$-C$_8$)-alkyl; and
n is a number from zero to two;
said compound being applied in a weight ratio of (0.1–5):1 with respect to said Fenoxaprop-ethyl.

2. A method as in claim 1 wherein said compound is applied in a weight ratio of (0.2–2):1 with respect to said Fenoxaprop-ethyl.

3. A method as in claim 1 wherein said compound is quinolyl-8-oxyacetic acid.

4. A method as in claim 1 wherein said compound is 5-chloro-quinolyl-8-oxyacetic acid.

5. A method as in claim 1 wherein said compound is methyl 5-chloro-quinolyl-8-oxyacetate.

6. A method as in claim 1 wherein said compound is methyl 5,7-dichloro-quinolyl-8-oxyacetate.

7. A method as in claim 1 wherein said compound is methyl quinolyl-8-oxyacetate.

8. A method as in claim 1 wherein said crop plant is wheat or barley.

9. A composition for combating grasslike weeds in crop plants, said composition consisting essentially of Fenoxaprop-ethyl, i.e. ethyl 2-[4-(6-chlorobenzoxazolyloxy)-phenoxy]-propionate and a compound of the formula

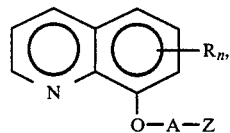

wherein
A is —CH$_2$— or —CH(CH$_3$)—;
R is halogen;
Z is —COOR$^1$;
R$^1$ H or (C$_1$-C$_8$)-alkyl; and
n is a number from zero to two;
in a weight ratio of said compound to said Fenoxaprop-ethyl of (0.1–5):1.

10. A composition as in claim 9 wherein the weight ratio of said compound to said Fenoxaprop-ethyl is (0.2–2):1.

11. A composition as in claim 9 wherein said compound is quinolyl-8-oxyacetic acid.

12. A composition as in claim 9 wherein said compound is 5-chloro-quinolyl-8-oxyacetic acid.

13. A composition as in claim 9 wherein said compound is methyl 5-chloro-quinolyl-8-oxyacetate.

14. A composition as in claim 9 wherein said compound is methyl 5,7-dichloro-quinolyl-8-oxyacetate.

15. A composition as in claim 9 wherein said compound is methyl quinolyl-8-oxyacetate.

* * * * *